(12) United States Patent  (10) Patent No.: US 7,575,728 B2
Holl et al.  (45) Date of Patent: Aug. 18, 2009

(54) PROCESSES EMPLOYING MULTIPLE SUCCESSIVE CHEMICAL REACTION PROCESS STEPS AND APPARATUS THEREFORE

(75) Inventors: Richard A. Holl, Camrarillo, CA (US); Eric A. Gulliver, Camarillo, CA (US); James E. Doss, Blountville, TN (US)

(73) Assignee: Kreido Laboratories, Camarillo, CA (US)

( * ) Notice: Subject to any disclaimer, the term of this patent is extended or adjusted under 35 U.S.C. 154(b) by 575 days.

(21) Appl. No.: 11/457,435

(22) Filed: Jul. 13, 2006

(65) Prior Publication Data

US 2006/0245991 A1 Nov. 2, 2006

Related U.S. Application Data

(62) Division of application No. 10/197,093, filed on Jul. 16, 2002, now Pat. No. 7,098,360.

(51) Int. Cl.
*B01J 8/04* (2006.01)
*B01J 10/00* (2006.01)
*B01J 19/00* (2006.01)
*B01J 19/18* (2006.01)

(52) U.S. Cl. .......................... 422/188; 422/224; 422/225
(58) Field of Classification Search ................. 422/188, 422/224, 225
See application file for complete search history.

(56) References Cited

U.S. PATENT DOCUMENTS 3,195,865 A  7/1965  Harder (Continued)

FOREIGN PATENT DOCUMENTS

DE  299 02 348  4/1999

(Continued)

OTHER PUBLICATIONS

PCT International Search Report for PCT/US00/18038, Holl Technologies Company, completed Sep. 17, 2000, mailed Oct. 6, 2000.

(Continued)

*Primary Examiner*—Walter D Griffin
*Assistant Examiner*—Natasha Young
(74) *Attorney, Agent, or Firm*—Greenberg Traurig, LLP

(57) ABSTRACT

The present disclosure provides processes and apparatus for the production of materials requiring a plurality of chemical reaction steps. In the prior art the number of reaction vessels is minimized by performing two or more reactions together in the same vessel. Instead each process is separated into separate successive steps, in each of which at least two principal components are reacted together, with or without at least one catalyst. In each step the components are reacted under optimum condition for that reaction, using motion-augmented, sub-Kolmogoroff, micro-agitation provided by a separate discrete motor-operated, micro-agitation means. Such means are much smaller in size, but are extremely flexible as to the flow rate and reaction conditions, so that they can be adjusted to suit the reaction, without compromises dictated by attempting to perform other reactions in the same vessel. Multiple micro-agitation means in parallel or in series can be used in each step to increase capacity without scale-up problems, and units can be serviced or capacity reduced without the need to close down the process. Motor-operated micro-agitation means performing a non-chemical action can be provided at any stage of the process. Between each two steps the resultant mixture is separated to give a principal component used in the subsequent step, while at least one new principal component is added in the next step.

3 Claims, 4 Drawing Sheets

U.S. PATENT DOCUMENTS

| | | |
|---|---|---|
| 4,106,439 A | 8/1978 | Kanao |
| 4,113,838 A | 9/1978 | Koike |
| 4,157,270 A | 6/1979 | Martignoni |
| 4,315,172 A | 2/1982 | Intichar et al. |
| 4,335,180 A | 6/1982 | Traut |
| 4,405,491 A | 9/1983 | Sando et al. |
| 4,438,082 A | 3/1984 | Dettling |
| 4,556,467 A | 12/1985 | Kuhn et al. |
| 4,593,754 A | 6/1986 | Holl |
| 4,670,103 A | 6/1987 | Holl |
| 4,708,198 A | 11/1987 | Holl |
| 4,744,521 A | 5/1988 | Singer et al. |
| 4,769,131 A | 9/1988 | Noll et al. |
| 4,778,631 A | 10/1988 | Cobbs, Jr. et al. |
| 4,784,218 A | 11/1988 | Holl |
| 4,793,247 A | 12/1988 | Verweij |
| 4,798,863 A | 1/1989 | Leland et al. |
| 4,889,909 A | 12/1989 | Besecke et al. |
| 4,917,462 A | 4/1990 | Lewis et al. |
| 4,921,473 A | 5/1990 | Lee et al. |
| 4,930,708 A | 6/1990 | Chen |
| 4,983,307 A | 1/1991 | Nesathurai |
| 5,154,973 A | 10/1992 | Imagawa et al. |
| 5,198,137 A | 3/1993 | Rutz et al. |
| 5,204,416 A | 4/1993 | Mercer et al. |
| 5,212,278 A | 5/1993 | Pfandner |
| 5,227,637 A | 7/1993 | Herold et al. |
| 5,268,140 A | 12/1993 | Rutz et al. |
| 5,270,998 A | 12/1993 | Uchiumi |
| 5,274,509 A | 12/1993 | Buch |
| 5,279,463 A | 1/1994 | Holl |
| 5,300,019 A | 4/1994 | Bischof et al. |
| 5,335,992 A | 8/1994 | Holl |
| 5,355,356 A | 10/1994 | Johann et al. |
| 5,358,775 A | 10/1994 | Horn, III |
| 5,370,824 A | 12/1994 | Nagano et al. |
| 5,370,999 A | 12/1994 | Stuart |
| 5,391,603 A | 2/1995 | Wessel et al. |
| 5,395,914 A | 3/1995 | Wilharm et al. |
| 5,422,872 A | 6/1995 | Hsu et al. |
| 5,431,955 A | 7/1995 | Kawamura et al. |
| 5,449,652 A | 9/1995 | Swartz et al. |
| 5,471,037 A | 11/1995 | Goethel et al. |
| 5,484,647 A | 1/1996 | Nakatani et al. |
| 5,506,049 A | 4/1996 | Swei et al. |
| 5,523,169 A | 6/1996 | Rafferty et al. |
| 5,538,191 A | 7/1996 | Holl |
| 5,552,210 A | 9/1996 | Horn, III et al. |
| 5,554,323 A | 9/1996 | Tsukimi et al. |
| 5,558,820 A | 9/1996 | Nagano et al. |
| 5,574,709 A | 11/1996 | Takeda |
| 5,576,386 A | 11/1996 | Kempter et al. |
| 5,602,819 A | 2/1997 | Inagaki et al. |
| 5,658,485 A | 8/1997 | Cava et al. |
| 5,658,994 A | 8/1997 | Burgoyne, Jr. et al. |
| 5,659,006 A | 8/1997 | White |
| 5,674,004 A | 10/1997 | Takeuchi |
| 5,693,742 A | 12/1997 | White et al. |
| 5,739,193 A | 4/1998 | Walpita et al. |
| 5,754,936 A | 5/1998 | Jansson |
| 5,855,865 A | 1/1999 | Lambert et al. |
| 5,874,516 A | 2/1999 | Burgoyne, Jr. et al. |
| 5,929,138 A | 7/1999 | Mercer et al. |
| 5,974,867 A | 11/1999 | Forster et al. |
| 5,998,533 A | 12/1999 | Weber et al. |
| 6,039,784 A | 3/2000 | Luk |
| 6,040,935 A | 3/2000 | Michalicek |
| 6,074,472 A | 6/2000 | Jachow et al. |
| 6,093,636 A | 7/2000 | Carter et al. |
| 6,134,950 A | 10/2000 | Forster et al. |
| 6,143,052 A | 11/2000 | Kiyokawa et al. |
| 6,176,991 B1 | 1/2001 | Nordman |
| 6,190,034 B1 | 2/2001 | Nielsen et al. |
| 6,281,433 B1 | 8/2001 | Decker et al. |
| 6,391,082 B1 | 5/2002 | Holl |
| 6,464,936 B1 | 10/2002 | Mowat et al. |
| 6,471,392 B1 | 10/2002 | Holl et al. |
| 2001/0030295 A1 | 10/2001 | Holl |
| 2002/0038582 A1 | 4/2002 | Holl |
| 2002/0078793 A1 | 6/2002 | Holl |
| 2002/0089074 A1 | 7/2002 | Holl |
| 2002/0148640 A1 | 10/2002 | Holl |
| 2003/0042126 A1* | 3/2003 | Nguyen et al. ........... 204/157.9 |
| 2003/0043690 A1 | 3/2003 | Holl |
| 2003/0066624 A1 | 4/2003 | Holl |

FOREIGN PATENT DOCUMENTS

| | | |
|---|---|---|
| DE | 299 19 570 | 1/2000 |
| EP | 0 219 357 | 4/1987 |
| EP | 0 660 336 | 6/1995 |
| GB | 612012 | 11/1948 |
| GB | 891 152 | 3/1962 |
| GB | 1 232 644 | 5/1971 |
| GB | 1 252 192 | 11/1971 |
| GB | 2 192 558 | 1/1988 |
| JP | 58 144549 | 8/1983 |
| JP | 3 279991 | 12/1991 |
| JP | 11322920 | 11/1999 |
| JP | 2000-213876 | 8/2000 |
| SU | 369 939 | 4/1973 |
| SU | 957 991 | 9/1982 |
| SU | 1 737 241 | 5/1992 |
| WO | WO 92 18213 | 10/1992 |
| WO | WO 95 06517 | 3/1995 |
| WO | WO 9530475 | 11/1995 |
| WO | WO 96 30113 | 10/1996 |
| WO | WO 97 12665 | 4/1997 |
| WO | WO 97 42639 | 11/1997 |
| WO | WO 98 49675 | 11/1998 |
| WO | WO 02 071451 | 9/2002 |
| WO | WO 03 022415 | 3/2003 |

OTHER PUBLICATIONS

PCT International Search Report for PCT/US01/15258, Holl Technologies Company, completed Jan. 24, 2002, mailed Feb. 1, 2002.

PCT International Search Report for PCT/US01/20635, Holl Technologies Company, completed Jan. 24, 2002, mailed Feb. 1, 2002.

PCT International Search Report for PCT/US01/23657, Holl Technologies Company, completed Apr. 25, 2002, mailed May 6, 2002.

PCT International Search Report for PCT/US02/11575, Holl Technologies Company, completed Jul. 12, 2002, mailed Aug. 6, 2002.

PCT International Search Report for PCT/US02/29093, Holl Technologies Company, completed Mar. 6, 2003, mailed Mar. 17, 2003.

PCT International Search Report for PCT/US02/31076, Holl Technologies Company, completed Dec. 11, 1002, mailed Dec. 27, 2002.

PCT International Search Report for PCT/US02/05361, Holl Technologies Company, completed May 17, 2002, mailed Jun. 5, 2002.

www.pooleplastics.com/production.html, Poole Plastics and Tooling Company, Production Capabilities; Feb. 15, 2001.

Zlotorzynski; "The Application of Microwave Radiation to Analytical and Environmental Chemistry;" Critical Reviews in Analytical Chemistry; vol. 25, No. 1; pp. 43-76; 1995.

"Microwave Heating Mechanisms;" Microwave Chemistry, (1994).

"A Basic Introduction to Microwave Chemistry;" Microwave Chemistry, (1997).

"Fast and Furious;" Microwave Chemistry, (1998).

"Microwave Heating Applied to Polymers;" Microwave Chemistry, (1994).

"Application of Microwaves to Organic Chemistry;" Microwave Chemistry, (1994).

"Microwave Chemistry in Liquid Media;" Microwave Chemistry, (1994).

"Microwave Heating and Intercalation Chemistry;" Microwave Chemistry, (1994).

US 6,159,264, 12/2000, Holl (withdrawn)

* cited by examiner

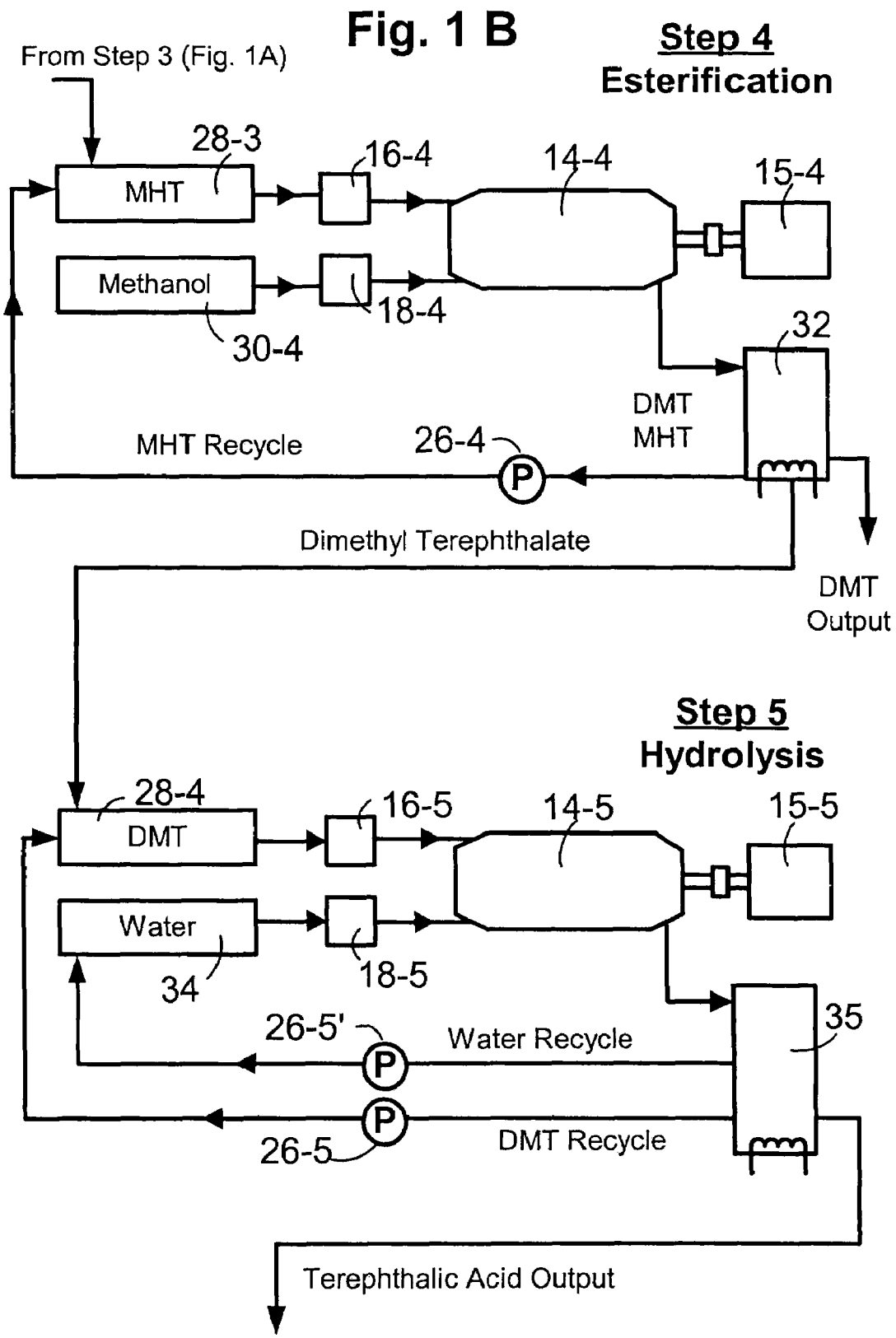

PROCESSES EMPLOYING MULTIPLE SUCCESSIVE CHEMICAL REACTION PROCESS STEPS AND APPARATUS THEREFORE

RELATED APPLICATION

This application is a divisional application and claims the benefit of and priority to of U.S. Utility patent application Ser. No. 10/197,093, filed Jul. 16, 2002 now U.S. Pat. No. 7,098,360, the contents of which are incorporated by reference herein in its entirety.

BACKGROUND

This present disclosure is concerned with new processes employing multiple successive chemical reaction process steps and apparatus therefore, and especially to such processes and apparatus employing micro-agitation to facilitate the chemical reactions carried out in the successive steps. The present disclosure is concerned especially, but not exclusively, with such processes and apparatuses for the production of organic dicarboxylic acids, and even more especially with such processes and apparatus for the production of dimethyl terephthalate and terephthalic acid.

SUMMARY

The present disclosure provides processes and apparatuses for the production of materials requiring a plurality of chemical reaction steps. In the past, the number of reaction vessels is minimized by performing two or more reactions together in the same vessel. Instead each process is separated into separate successive steps, in each of which at least two principal components are reacted together, with or without at least one catalyst. In each step the components are reacted under optimum condition for that reaction, using motion-augmented, sub-Kolmogoroff, micro-agitation provided by a separate discrete motor-operated, micro-agitation means. Such means are much smaller in size, but are extremely flexible as to the flow rate and reaction conditions, so that they can be adjusted to suit the reaction, without compromises dictated by attempting to perform other reactions in the same vessel. Multiple micro-agitation means in parallel or in series can be used in each step to increase capacity without scale-up problems, and units can be serviced or capacity reduced without the need to close down the process. Motor-operated micro-agitation means performing a non-chemical action can be provided at any stage of the process. Between each two steps the resultant mixture is separated to give a principal component used in the subsequent step, while at least one new principal component is added in the next step. Micro-agitation processes and the micro-agitation means therefore are described in U.S. Pat. Nos. 5,279,463 and 5,438,191 and application Ser. No. 09/802,037 entitled Method and Apparatus for Materials Processing. The materials to be produced preferably comprise organic di-carboxylic acids, and more preferably dimethyl terephthalate and terephthalic acid.

The present disclosure discloses an apparatus for the production of materials requiring a plurality of chemical reaction steps, wherein the process for which the process apparatus is employed has been separated into a plurality of separate successive process steps, each process step involving the reaction together of at least two principal step reaction components, with or without at least one catalyst component; wherein each process step is carried out in a separate, respective process step apparatus comprising: (a) motor-operated, micro-agitation means; (b) means for feeding the respective principal step reaction components to the motor-operated micro-agitation means wherein they are reacted together while subjected to motion-augmented, sub-Kolmogoroff, micro-agitation to facilitate the reaction between them, the operation of the motor-operated micro-agitation means resulting in a mixture of process step output materials; and (c) means for discharging such a mixture therefrom; and wherein each process step apparatus also comprises: (a) process step separator means for separating from the mixture of process step output materials received from the micro-agitation means a principal step reaction component for supply to a subsequent process step apparatus; (b) means for feeding a mixture discharged from the micro-agitation means to the process step separator means; and (c) means for discharging at least the separated principal step reaction component from the process step separator means for supply to the subsequent process step apparatus.

DRAWINGS

The above-mentioned features and objects of the present disclosure will become more apparent with reference to the following description taken in conjunction with the accompanying drawings wherein like reference numerals denote like elements and in which:

FIGS. 1A and 1B together are a schematic representation of such processes, more specifically a process for the production of dimethyl terephthalate and terephthalic acid;

The same or corresponding components and parts are given the same reference number wherever possible, appropriate suffixes being used where necessary to indicate any differences.

DETAILED DESCRIPTION

Figure 1A:
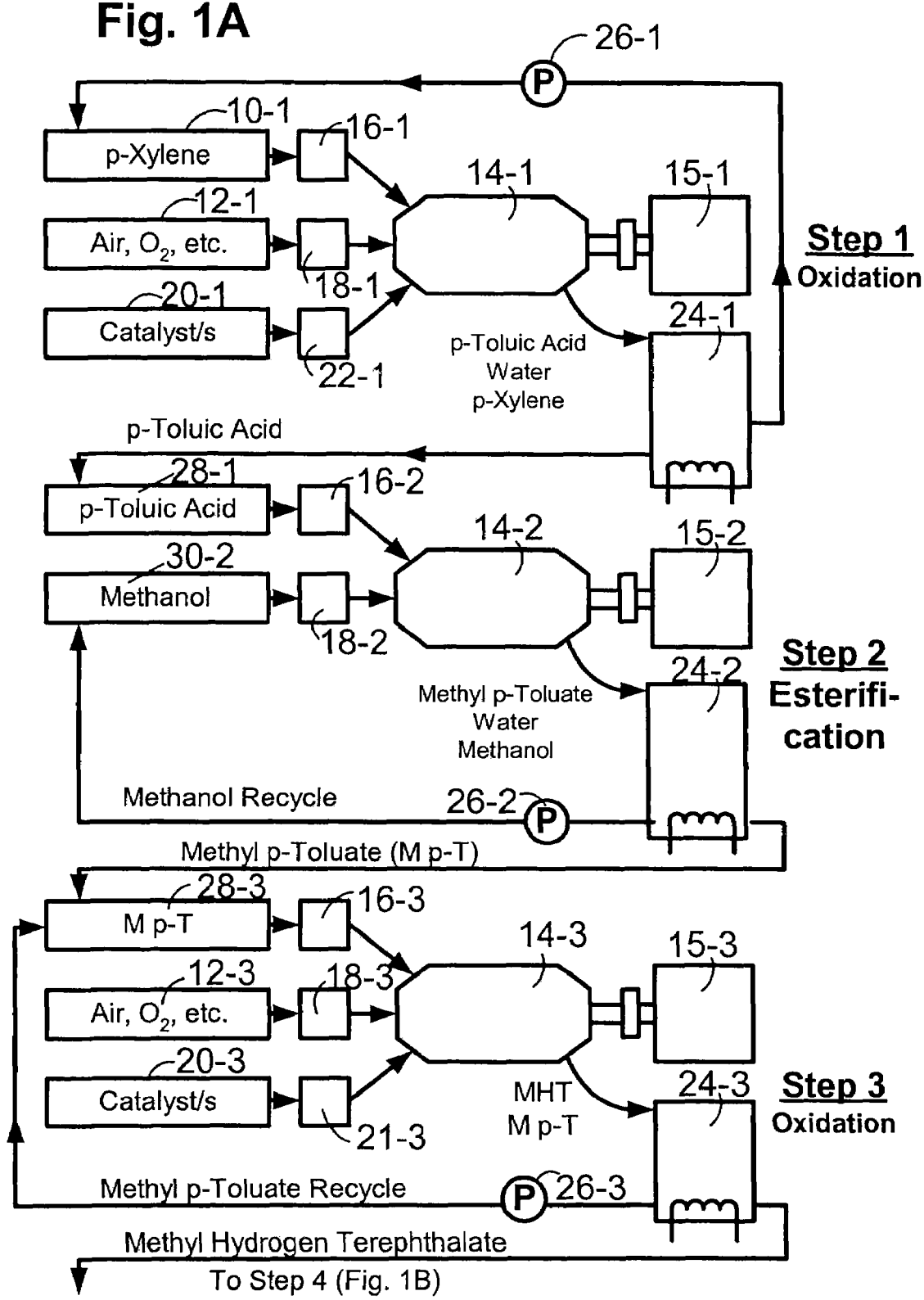

An example of a large group of industrial processes that involve a number of different chemical reactions taking place simultaneously in large, expensive reactor vessels are those involved in the production of organic carboxylic acids, particularly terephthalic acid (TPA). TPA is a major industrial chemical product, its principal application being the manufacture of various polymers, particularly polyethylene terephthalate (PET), which has widespread use in the production of synthetic fibers, fabrics and films, and particularly the production by blow molding of transparent food and drink containers. Owing to the quantities required, the production of TPA is carried out in large installations in order to achieve economy of scale, the reaction vessels and associated equipment employed being correspondingly very large and expensive. The currently available processes involve a number of different reactions, and it is common to carry out at least some of the reactions simultaneously in a single vessel, in order to reduce the amount of the large, complex, and expensive equipment required. The simultaneous performance of such reactions generally means that the conditions of temperature, pressure, and concentration within the reactor vessel or vessels is a compromise between those that otherwise would be preferred for the different reactions.

Another result of the need to operate with large size installations (e.g., a plant for TPA production must have a capacity of at least 100,000 tonnes per annum) is that it has become a major financial decision to begin construction of a new plant, or expansion of an existing plant, when current production becomes insufficient. When the new plant, or expansion, comes online, the problem then arises that for a considerable period, which may be as long as several years, there is overproduction which depresses the available price and considerably extends the period required before both the new and the existing plants again become sufficiently profitable. The problem is exacerbated if two or more producers decide at about the same time to expand capacity. A corresponding situation arises when there is a down-turn in the economy necessitating a reduction in production. Producers are faced with the unwelcome choice of keeping a plant operating, resulting in overproduction and lowered price, or to shut down completely, an expensive process with attendant labor difficulties and with resultant inadequate production. Again, the situation is exacerbated if two or more producers make the same decision at about the same time.

As stated in "Industrial Organic Chemistry-Important Raw Materials and Intermediates" of Klaus Weissermel and Hans-Jurgen Arpe, 3nd edition published 1997 by Verlag Chemie, the simplest method to produce PET is the polycondensation via direct esterification of TPA and ethylene glycol method, but only if the TPA is of the so-called "fiber grade" of purity. For example, in order to be suitable for the preparation of polyester fibers the TPA must be substantially free of contaminants which lower the melting point of the polyester or cause the formation of color bodies. Some impurities in crude TPA, such as 4-carboxybenzaldehyde, are color-forming precursors and can also act as chain terminators preventing the production of polymers of sufficiently high molecular weight. These impurities are difficult to remove from crude TPA, owing to the very low solubility of TPA in polar solvents such as water or glacial acetic acid, even at elevated temperatures and pressures. An early process to obtain TPA of high purity involved converting the crude TPA to the dimethylester, which could economically be brought to fiber grade quality by crystallization or distillation. Older, less energy-efficient PET processes employing DMT have largely been superseded by more modern facilities that use the purified TPA in a direct esterification, rather than the lower-yielding, slower-reacting DMT transesterification processes.

A common first stage in the production of TPA is the liquid phase oxidation of p-xylene in large vessels in which the contents are agitated, typically at temperatures in the range 100-200° C., sometimes in the range 140-170° C., and at pressures in the range 4-20 bar, sometimes 4-8 bar, and with residence times in the reactor vessels of up to 22 hours. The oxidation stops at the stage where p-toluic acid (one methyl group, one carboxyl acid group) is produced, unless special steps are taken to convert the second methyl group to a carboxyl acid group. There are three main ways in which this has been achieved; many others have been used and proposed but they are of lesser commercial importance.

In a first method, the carboxyl group of the p-toluic acid is esterified with methanol, whereupon subsequently the second methyl group can be oxidized. It is usual to use the methanol as a solvent during the oxidation, so that the esterification occurs simultaneously with the oxidation in a single reaction vessel. The method yields dimethyl terephthalate which, after separation and purification to fiber grade, is hydrolyzed readily to TPA.

In a second method, now usually referred to as the Amoco process, and the predominant process for the manufacture of TPA, a metal salt catalyst, usually a mixture of manganese and cobalt acetate in 95% acetic acid, is employed, together with a co-catalyst or promoter such as ammonium bromide and tetrabromoethane, or a mixture of manganese and cobalt bromides, the bromine ion functioning as a regenerative source of free radicals that continue the oxidation. Temperatures of 190-205° C. and pressures of 15-30 bar are employed; the reaction vessels are extremely large and, together with the associated equipment, must be lined or made with materials able to withstand the corrosive attack of the bromine ions, so that they are correspondingly initially expensive and costly to maintain. Typically titanium or Hastelloy CTM alloys are employed. The TPA obtained must be purified and this is done by dissolving it under pressure at 225-275° C. in water and hydrogenating the solution in the presence of a platinum/charcoal catalyst, whereby the chief impurity, 4-carboxylbenzaldehyde, is hydrogenated to p-toluic acid. The pure TPA crystallizes out upon cooling the solution. The process is also suitable for oxidizing other methylbenzenes and methylnaphthalenes to aromatic carboxylic acids, e.g. toluene to benzoic acid; m-xylene to isophthalic acid; pseudocumene to trimellitic anhydride; mesitylene to trimesic acid; and 1,4-dimethylnaphthalene to naphthalene-1,4-dicarboxylic acid.

The third method, which is no longer in commercial use, is a co-oxidation process in which the principal reactions are all carried out together in a single vessel. Thus, the oxidation is carried out in the presence of an auxiliary substance which is simultaneously oxidized, and that is capable of supplying hydroperoxides that will complete the oxidation process. In one typical process, p-xylene together with paraldehyde and cobalt acetate in acetic acid solution, are introduced at the head of a tall (e.g. 30 meters) bubble column, while air is introduced at the bottom, a typical temperature being 100-140° C. and a typical pressure being 30 bar. The bubbles ascending in the column are relied upon to produce the necessary interaction and chemical reaction between the components. The TPA is removed as a suspension in the acetic acid, separated, and purified.

Referring now to FIG. 1, the process illustrated therein is primarily for the production of the organic dicarboxylic acid terephthalic acid (TPA), but does have as an intermediate step the production of dimethyl terephthalate (DMT). The process has been separated for the application of the present disclosure into five separate successive process steps, the first four of which result in the production of the DMT, and in the fifth of which the DMT is converted to TPA.

In the first step, two principal first step reaction components are fed together by respective feed means from respective sources 10-1 and 12-1 thereof into a respective first motion-augmented micro-agitation means 14-1 driven by a respective motor 15-1, the structure and operation of which will be described below. One of the principal components is a liquid, namely p-xylene. The other is a gas selected from the group consisting of air, oxygen enriched air, and pure oxygen. The two components react together in an oxidation reaction facilitated by the operation of the micro-agitation means to produce a mixture of p-toluic acid, water, and any unreacted p-xylene. The p-xylene is fed to the micro-agitation means via an accurately metered pump 16-1 to obtain the volume and pressure required, usually in the range 10-30 bar, and is also at the temperature required, usually in the range 120-190° C. The oxygen or oxygen-containing component can be fed directly via a meter 18-1 from the source 12-1 in which inherently it will be under pressure.

In all prior processes, the reaction typically requires the use of a catalyst, as described above, a mixture of the acetate salts of manganese and cobalt together with bromine containing compounds as a co-catalyst. Such catalysts are fed from a source 20-1 thereof to the interior of the micro-agitation means at the required temperature and pressure by an accurately metered pump 22-1. Again, as in the Amoco process described above, the bromine free ions make the resulting reacting mixture highly corrosive and their presence usually necessitates the use for the apparatus of corrosion resistant materials, such as relatively pure titanium or high-nickel content alloys. The micro-agitation means is of small size for its output, as compared to the very large stirred or bubble tanks employed in the prior processes, and is therefore very cost effective in that regard. Owing to the motion-augmented, sub-Kolmogoroff, micro-agitation that is applied to the mixture by the micro-agitation means the amount of such catalysts and co-catalysts required may be substantially reduced or even eliminated, owing to the greater efficiency of operation under the high rates of surface renewal to which the reacting materials are subjected.

The use of meters in the supply of the various reaction components to the micro-agitation means is desirable in view of the high reaction rates achievable, so that the components can be supplied as closely as possible in the optimum ratio for the reaction. The reaction is strongly exothermic and the usual way to remove the excess heat is to employ an excess of the p-xylene, which subsequently is flashed away from the rest of the reaction mixture, for example by condensing the evaporated p-xylene in a condenser attached to the flash column. Excess heat can also be removed from the micro-agitation means via a heat exchanger comprising a heat exchange jacket surrounding the machine and associated heat exchange means that supplies heat exchange fluid to the jacket interior, so that both the temperature and pressure under which the reaction takes place can be controlled to be within optimum ranges of values. If the reaction is endothermic then of course the heat exchanger is arranged to supply the heat required. Ideally, if possible, the overall process is operated to minimize the need for interstage heating or cooling, since the provision of the necessary added equipment adversely affects the economics of the process.

Some prior processes have attempted to minimize the number of the expensive reaction vessels required by adding to the reaction mixture materials, such as acetaldehyde, paraldehyde and methyl ethyl ketone, that will be co-oxidized and produce a combined esterification and oxidation reaction, but this is not done in the processes of the present present disclosure and instead it is preferred to employ separate, discrete, individual steps each involving a separate chemical reaction, so that they are relatively independent of one another, and which can therefore be made as efficient as possible, without the need to compromise the conditions under which they operate to take account of the other reactions also taking place.

The mixture of process step output materials is in this embodiment fed to a first step flash system, such as flash column 24-1, in which the p-toluic acid, water and residual p-xylene are separated in respective vapor streams and condensed, the p-xylene being recycled to the feed source 10-1, a recycle pump 26-1 being provided if required, and thence into the first step micro-agitation means 14-1 after being decanted from the water that is produced in the process. The p-toluic acid may be fed to a reservoir 28-1 in which its temperature can be adjusted to be within the range preferred for a second step of the overall process in which it is esterified to its monomethyl ester, this reservoir and its contents then constituting a source for a principal reaction component of the immediately succeeding step.

In this second step, or stage, the separated p-toluic acid becomes one of two principal second step reaction components that are fed to a second micro-agitation means 14-2, the feed taking place via a metered pump 16-2 so that the input pressure and flow rate can be controlled to optimum input pressure values and optimum proportions, which in some reactions will be in the stoichiometric ratio for that reaction. The second principal second step reaction component is methanol and this may be fed from a source reservoir 30-2 in which its temperature is adjusted, as with the p-toluic acid to be within an optimum range for the reaction, the feed also being via a metered pump 18-2. As indicated above, in this step the p-toluic acid is esterified in the presence of the methanol to methyl p-toluate, so that the process step output mixture from the micro-agitation means consists of the methyl p-toluate, water and unreacted methanol, the latter again being minimized in view of the use of optimum temperature and pressure and the optimization of the ratio of the materials fed into the second micro-agitation means 14-2. As in the first step process, the temperature within the micro-agitation means is controlled if and as required by a corresponding heat exchange system to remain within the chosen optimum range. Again, as before, the mixture of process step output materials from the second micro-agitation means is fed to a flash system 24-2 in which the components are separated in respective vapor streams and condensed, the methanol being recycled to the feed reservoir 30-2, via a pump 26-2, if necessary, and then back into the second step micro-agitation means. The methyl p-toluate is fed to a second step reservoir 28-2 in which its temperature can be adjusted to be within the range required for a third step of the overall process, in which the methyl p-toluate ester is oxidized to the methyl hydrogen terephthalate.

In the third step, or stage, the separated methyl p-toluate becomes one of two principal third step reaction components that are fed to a third micro-agitation means 14-3, the feed taking place via a metered pump 16-3 as before so that the pressure and flow rate can be controlled appropriately. The second principal third step reaction component is again selected from the group of air, oxygen enriched air, and pure oxygen fed from a supply 12-3 of the required input pressure. The reaction in this third step is more likely than that in the first step to require the use of a catalytic component, such as those referred to above in the description of the first step, so that again it may be necessary to construct the machine of suitable corrosion resistant materials. The catalysts and promoters again are fed to the interior of the third micro-agitation means from a source 20-3 via an accurately metered pump 21-3. In this step the methyl p-toluate is oxidized to methyl hydrogen terephthalate, the process step output mixture consisting of the methyl hydrogen terephthalate, water and unreacted methyl p-toluate, the latter again being minimized in view of the optimized ratio of the materials fed under optimum conditions of temperature and pressure into the micro-agitation means. As in the first step process, the temperature within the third micro-agitation means is controlled to remain within an optimum range. Again, as before, the mixture of third process step output materials from the micro-agitation means 14-3 is fed to a flash system 24-3 in which the various components are separated in respective vapor streams and condensed, the methyl p-toluate being recycled via a pump 26-3 to the feed reservoir 28-2 and thence into the third step micro-agitation means 14-3. The methyl hydrogen terephthalate is fed to a third step reservoir 28-3 in which its temperature can be adjusted to be within the range required for a fourth step of the overall process, in which the methyl hydrogen terephthalate is esterified to dimethyl terephthalate (DMT).

In the fourth step, or stage, the separated methyl hydrogen terephthalate becomes one of two principal step reaction components that are fed to a fourth step micro-agitation means 14-4, the feed taking place via a metered pump 16-4 as before so that the pressure and flow rate can be controlled appropriately. The second principal step reaction component is again methanol within the optimum temperature range, which is fed from a source 30-4 thereof into the micro-agitation means via metered pump 12-4 to obtain the required input volume and pressure. The esterification reaction in this fourth step results in the production of dimethyl terephthalate, the process step output mixture from the fourth micro-agitation means consisting of the dimethyl terephthalate, water, and unreacted methyl hydrogen terephthalate, the latter again being minimized. As in the previous step processes, the temperature within the fourth micro-agitation means is controlled by a corresponding heat exchange system to remain within an optimum range. The mixture of output materials from the fourth micro-agitation means is fed to crystallizer or drum flaker 32 in which the various components are separated. The newly generated dimethyl terephthalate is purified by conventional means, while the unreacted methanol is recycled via pump 26-4 to the feed reservoir 28-3 and thence into the fourth step micro-agitation means. The dimethyl terephthalate which results is itself an industrial product used for example in the production of polymers, and some processes will terminate with the purified material.

The process can be terminated to result in crude terephthalic acid by making the fourth step a hydrolysation step in which the methyl hydrogen terephthalate is directly hydrolysed with water in place of the esterification as set out above.

DMT is a preferred precursor in processes for the production of TPA since it is relatively easy to purify, whereas this is not the case with TPA principally, as described above, owing to the relative insolubility of TPA in solvents other than hot, highly pressurized water or glacial acetic acid. In the fifth step of this overall process the purified crystallized DMT becomes one of two principal step reaction components that are fed in the form of a solution, suspension, or slurry from a source 28-4 to a fifth micro-agitation means 14-5, the feed taking place via a metered pump 16-5 as before so that the pressure and flow rate can be controlled appropriately. The second principal step reaction component is demineralized water fed into the micro-agitation means via a metered pump 18-5 from a suitable source 34 thereof. As in the previous step processes, the temperature within the fifth micro-agitation means is controlled if and as required by a corresponding heat exchange system to remain within an optimum range. The hydrolysis reaction in this fifth step results in the production of TPA which is separated from the water in a separator 35 to be in a relatively pure form, e.g., with impurities such as 4-carboxybenzaldehyde below a required minimum. The process step output mixture from the fifth micro-agitation means consists of the terephthalic acid, water and unreacted dimethyl terephthalate, the latter again being minimized in view of the optimum conditions and optimized ratio of the materials fed into the micro-agitation means.

Figure 2:
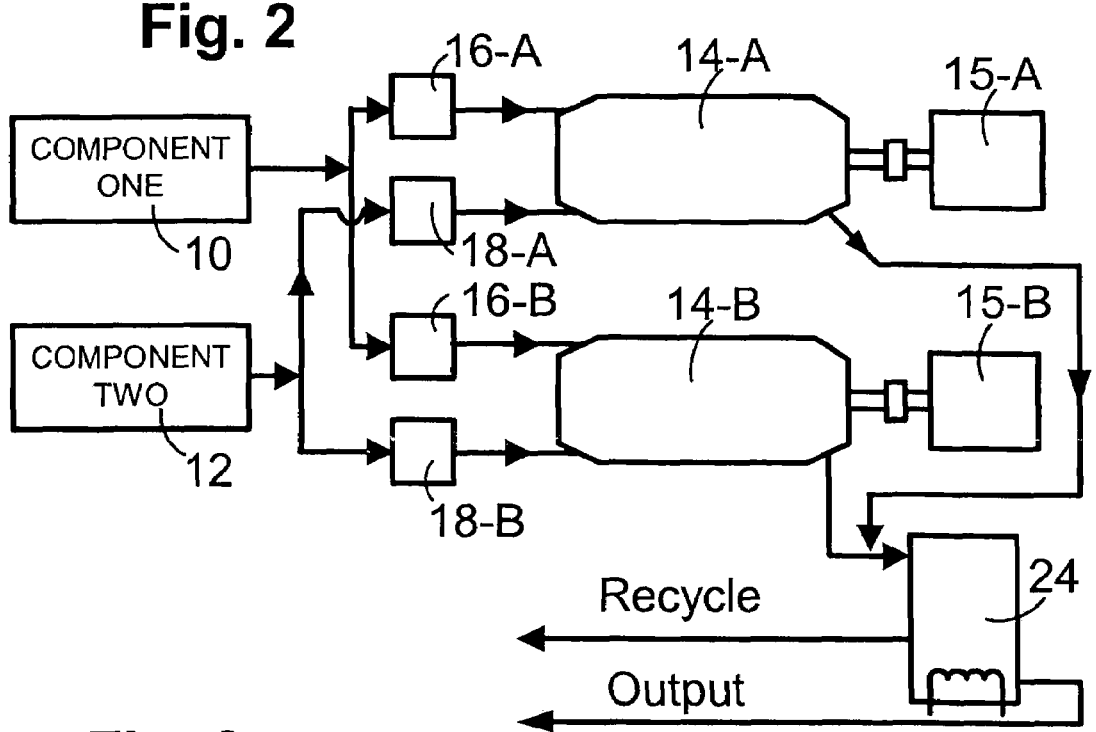
FIG. 2 is a schematic representation of one step or an overall process in which two motor-operated micro-agitation means are operated in parallel.
Figure 3:
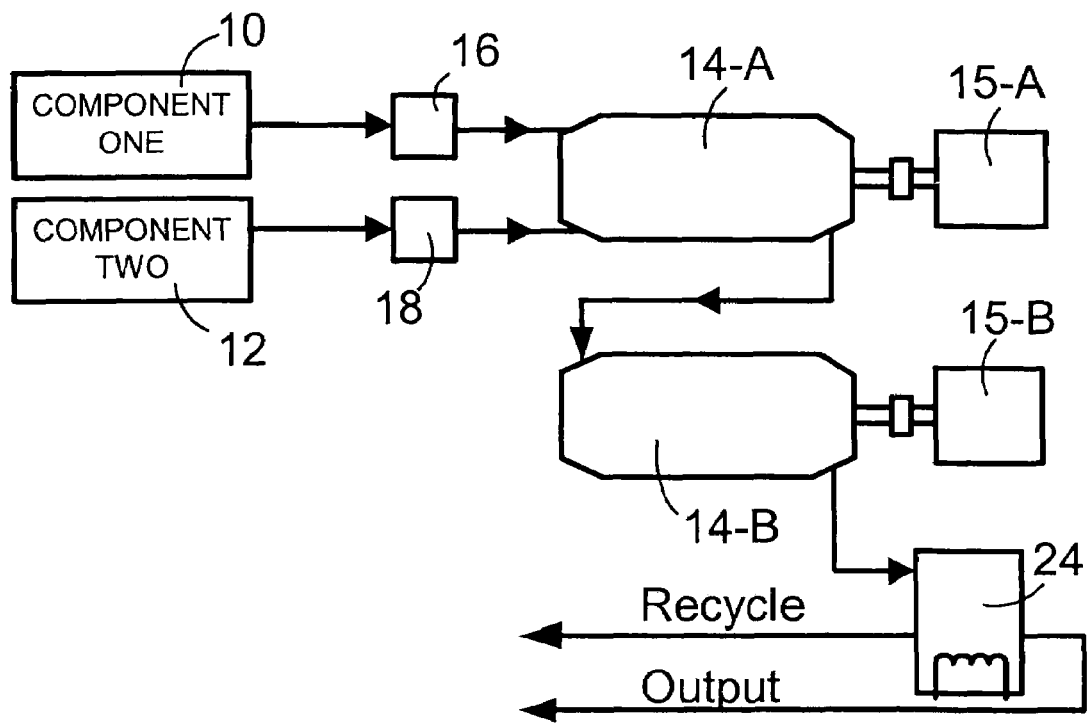
FIG. 3 is a schematic representation of one step or an overall process in which two motor-operated micro-agitation means are operated in series.

It is an unexpected advantage of the use of micro-agitation means as employed with this present disclosure that the dimensions of each apparatus can be predetermined to provide, within limits, the flow rate and residence time required for each reaction to proceed to completion while in the machine, if that is at all possible. This, together with the accurate control of temperature and pressure, minimizes the possibility of unwanted side reactions and the presence in the discharge of excessive amounts of unreacted material. If it is not possible to provide the required flow rate, etc., in a single machine then there is no difficulty in providing as many machines as are required connected in parallel. Such a step is illustrated by FIG. 2, in which two machines 14A and 14B are supplied from common component sources 10 and 12 via metered pumps 16A, 16B, 18A and 18B, and deliver their outputs to a common reservoir, flash system, crystallizer, etc., indicated by reference 24. If the residence time in a single machine is insufficient for the reaction to proceed to completion there is no difficulty in connecting two or more machines in series, and this is illustrated by FIG. 3, in which the two machines 14A and 14B are in series, with machine 14A receiving the components from sources 10 and 12 via respective metered pumps 16 and 18, and with machine 14B delivering its output to the reservoir, etc. 24. The opportunity is also provided of having in any such cluster of machines at least one additional machine that can be brought into service if any of the cluster requires service or standard maintenance, without the need to shut down the entire process. Since even a small scale industrial size operation is likely to require in each step a number of machines operating in parallel or series to obtain the necessary flow rate, etc. it is a simple matter to provide in each step one or two additional machines for this purpose. A further advantage is that if the full production capacity is not required at any time for a short period or even an extended period, this is handled very simply by taking one or more machines in each step out of service until the desired lower capacity is obtained. When full output is required it can be restored just as easily.

A further advantage of the present disclosure is the possibility of providing standard reaction modules, each of which is capable of carrying out a specific chemical reaction, and which can then be connected in series or parallel to carry out a multi-step reaction. Such modules, for example, simplify the assembly of a pilot plant since all that is required is to select the size of module required and connect a number of them together as needed. The design thereafter of a full-scale plant is simplified, since there are no scale-up problems as with the prior stirred and bubble tank installations, and all that is required is to select the required number of units that are to be assembled and operated together. Such a module will comprise, for example, at least three reservoirs as sources for the components, associated metered feed pumps, a micro-agitation machine of corresponding capacity, and a reservoir or reservoirs to receive the reacted mixture.

In the processes described above all of the process steps involve a respective multi-reactant chemical reaction, but there are a large number of such processes, as well as single reactant or component processes, in which one or more of the steps into which the processes are divided does not comprise a chemical reaction and instead may be characterized as a physical operation, such as the production of emulsions, suspensions, and solutions. Such physical and single component processes often can with substantial advantage make use of motion-augmented, sub-Kolmogoroff micro-agitation, as provided by the motor-operated, micro-agitation means, especially when such actions require close and uniform control of the conditions to which the process components are subjected. Other examples are polymerizations in which strong agitation conditions are required as the polymerization proceeds and viscosity increases to enable the reaction to more rapidly achieve the desired molecular weight, useful decompositions and degradations of starting materials under controlled conditions of heat, pressure, and shear (e.g., caramelization of corn syrup), and rearrangement of molecular structure to provide different isomers and proportions of isomers, or ring openings or closings. Any number of such additional steps or stages may be provided, each of which can, without limitation, but by way of example only, be disposed in the process sequence at a location selected from the group comprising prior to all of the process steps, prior to any of the process steps involving a reaction, subsequent to any of the process steps involving a reaction, subsequent to all of the process steps, and interposed between any two successive process steps involving a reaction.

Figure 4:
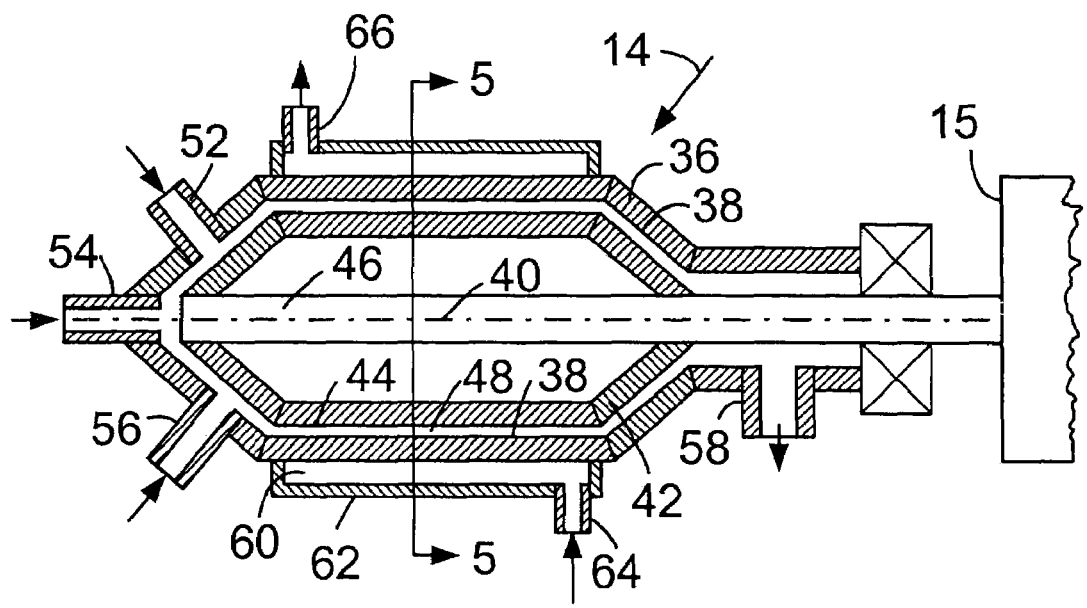
FIG. 4 is a longitudinal diagrammatic cross-section through a motion augmented, sub-Kolmogoroff, micro-agitation means as preferably employed as apparatus of the present disclosure.
Figure 5:
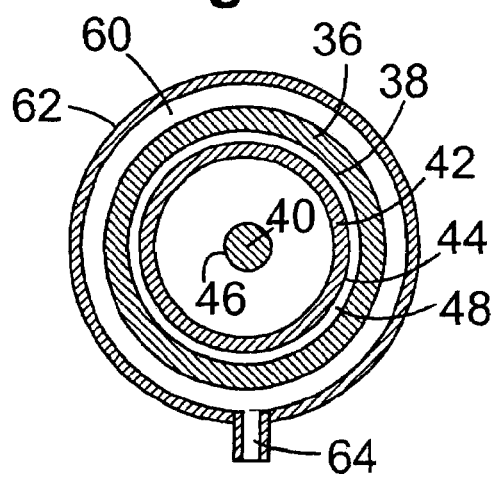
FIG. 5 is a transverse cross-section of the apparatus of FIG. 4, taken on the line 5-5 therein.
Figure 6:
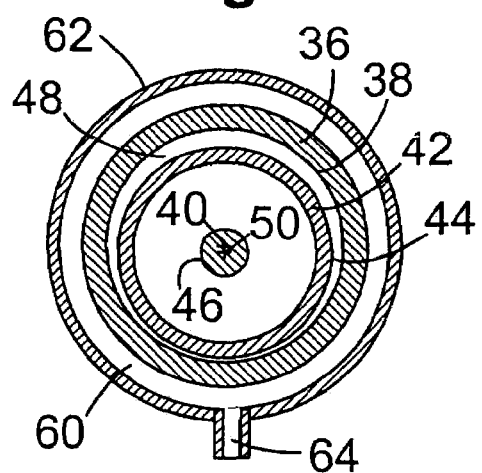
FIG. 6 is a transverse cross-section, similar to FIG. 3, through such an apparatus in which its operative stator and rotor cylindrical surfaces have respective longitudinal axes that are parallel and slightly displaced from one another.

Motor-operated micro-agitation means as employed in the processes and apparatus of this present disclosure are described and claimed, for example, in prior U.S. Pat. Nos. 5,279,463 and 5,438,191 and in application Ser. No. 09/802,037 entitled Method and Apparatus for Materials Processing, the disclosures of which are incorporated herein by this reference. Referring now to the diagrammatic drawings FIGS. 4-6, and first to the embodiment shown in FIGS. 4 and 5, such apparatus comprises essentially a cylindrical stator tube 36 having at least a part along its length of uniform internal diameter to provide a corresponding inner cylindrical surface 38 struck about a central longitudinal axis 40. A rotor 42 is mounted for rotation within the tube with its longitudinal axis precisely coextensive with the tube axis 40, so that its outer cylindrical surface 44 is parallel to the inner tube surface 38. A rotor shaft 46 is connected to an electric motor 15 by which it is rotated about the common tube/rotor axis. As usually manufactured the rotor also comprises a tubular member and the machine may therefore be referred to as a spinning tube in tube reactor, more specifically referred to as an STT (Trademark) reactor. The longitudinally extending annular space 48 between the relatively moving tube inner surface 38 and the rotor outer surface 44 provides a passage comprising or containing what may be variously described as a micro-mixing zone, a micro-agitation zone, or a treatment gap, passage, or chamber, which, when the axes about which the surfaces are struck are coincident, as in this embodiment, is of constant radial dimension about its circumference. In an alternative form of the apparatus illustrated by FIG. 6 the tube axis 40 and the rotor longitudinal axis 50 are parallel but are displaced by a small amount from one another, so that the annular treatment passage 48 is eccentric with its radial dimension varying between a specific minimum and maximum, the portion which surrounds the minimum being the micro-agitation zone.

Material to be treated is fed into this passage 48 via one or more inlets 52. 54 and 56, usually a different material through each inlet, and the micro-agitated material exits through one or more outlets 58. In practice it is unusual for a physical or chemical reaction to proceed isothermally, with the result that the material in the annular passage, as well as the inner tube wall surface are cooled or heated. It is also usual that for optimum efficiency in carrying out the process the temperature of the material being processed must be maintained in a range between certain limits, which can be quite critical and narrow and correspondingly difficult to achieve. It is usually necessary therefore to provide the apparatus with some means for supplying heat energy to the treatment zone, or with some means for removing heat energy as it is generated, and such means must of course provide adequate heat exchange capacity if a temperature within the required range is to be maintained. To this end, the wall of the stator tube 36 is made as thin as possible, and of as high heat conductivity as possible, and an annular passage 60 is formed around the exterior surface of the tube by a casing 62. Heat exchange fluid is fed to the passage 60 through one or more inlets 64 and is removed through one or more outlets 66. High capacity heat exchange apparatus, particularly intended for use in such micro-agitation machines, are described, for example, in U.S. application Ser. No. 60/318,985 entitled Method and Apparatus for Radial Impingement Heat Transfer, the disclosure of which is incorporated herein by this reference.

The annular gap 48 between the opposed tube and rotor surfaces is of very small dimensions, as will be described below, in which the micro-agitation processing that is taking place is independent of "volume" effects, being constituted instead by the interaction of boundary layer films, with or without a very thin intervening layer, of the materials on the opposed surfaces. Thus, immediately upon entry of the materials into the annular space very large interfacial contact areas are produced which are subject to extreme rates of surface renewal. Unusually high fluid shear rates can be created which, due to the confinement of the material in a gap whose radial dimension is at most a few millimeters, and sometimes measured in microns, results in the creation of vortices of correspondingly small dimension which drastically enhance mass, heat and momentum transfer. Conventional bulk volume stirring apparatus, even when of "high-shear" design, always exhibits the property that initially the mixing proceeds quite quickly and then slows drastically, so that many processes can take several days of continuous stirring. It was first shown by Dr. A. N. Kolmogoroff that this was the result of the generation of very small eddies of minimum size of about 10-20 microns diameter in the liquid body in which the particles to be distributed, that usually are smaller than this, became entrained so that the mechanical shear was no longer effective, and further mixing, etc. was the result of very much slower "molecular" effects. When the chamber is of uniform radial dimension around its circumference that dimension is made sufficiently small that these Kolmogoroff vortices are suppressed, and any eddies that can be produced are much smaller and are therefore referred to as "sub-Kolmogoroff" vortices, while the mixing that is obtained is referred to as motion-augmented, sub-Kolmogoroff, micro-agitation. When the chamber is eccentric in radial dimension at least one part around its circumference is of sufficiently small radial dimension that it constitutes a high-shear treatment zone in which free Kolmogoroff eddies and supra-Kolmogoroff eddies are suppressed during passage of the material there through. Such apparatus provides treatment methods that are operable, for example, to quickly forcibly dissolve gases and solids in liquids in which they are normally of low solubility, or to virtually instantaneously emulsify non-miscible liquids, or to chemically react two or more materials together with very high reaction rates.

Micro-agitation processing apparatus as described above takes advantage of the special properties of the boundary layer that is always present whenever a viscous fluid is in contact with a surface, together with the interaction that can be produced between two boundary layers on two relatively moving surfaces, namely the stator inner surface 38 and the rotor outer surface 44, when those surfaces are sufficiently close together for the two boundary layers to interact. The type of flow obtained between two such surfaces has been well described by G. I. Taylor, who showed that when a certain Reynolds number was exceeded the previously stratified flow in the annular space became unstable and vortices appeared, now known as Taylor vortices, whose axes are located along the circumference of the rotor parallel to its axis of rotation, and which rotate in alternately opposite directions. The conditions for the flow to become unstable in this manner can be expressed with the aid of a characteristic number known as the Taylor number, depending upon the radial width of the annular gap, the radius of the rotor, and its peripheral velocity. The presence of these Taylor vortices inhibits the processing desired, since the material to be treated becomes entrained in them and consequently at least partially segregated, whereupon high-shear mixing again becomes impossible and instead much slower molecular diffusion processes predominate.

As material being processed flows in the annular chamber a respective boundary layer forms on each of the stator and rotor cylindrical surfaces the thickness of which is determined by the viscosity and other factors of the material and the relative flow velocity of the material over the surfaces. The thickness δ of a laminar boundary layer for a fluid flowing over a flat surface along a path length X, which in this apparatus may be taken as one circumferential flow length around the rotor surface, may be determined by an equation comprising 4.91 times X divided by the square root of $N_{RX}$, which is the product of length X and the flow velocity divided by the kinematic viscosity. The diameter of the internal stator surface and the diameter of the external rotor surface are such that the radial dimension of the entire processing chamber, or that of the processing portion when the radial dimension varies, is at most about equal to the combined thicknesses of the two boundary layers back-to-back, so that there is no room between them for an intervening bulk layer such that would permit Taylor vortices to be formed and disrupt the high-shear mixing. As a specific example, with apparatus in which the rotor circumference X was 0.2394 meters, in which the rotor rotated at 2,000 revolutions per minute, and in which the kinematic viscosity was 0.000001 $m^2$/sec, the thickness δ of a single laminar boundary layer was 0.85 mm, and that of back to back interacting boundary layers 1.7 mm. It is will be noted that these dimensions are independent of the diameters or lengths of the two cooperating surfaces, and therefore there is neither a scale up or a scale down problem respectively in enlarging or reducing the size of the apparatus. Similarly, residence times within the chamber can easily be adjusted by changing its length, any increase being subject only to the mechanical problems that may be encountered in maintaining the radial dimension of the passage sufficiently constant when the rotor becomes over-long.

Other examples of multi-step chemical reactions in which the processes and apparatus of the present disclosure can be used are in general the production of aromatic carboxylic acids from methyl benzenes other than p-xylene and also from methylnaphthalenes. For example, m-xylene can be used as a starting material and the same route followed of oxidation in a first step of one methyl group to a carboxylic acid group, esterification of the oxidized group in a second step, oxidation in a third step of the second methyl group to the corresponding carboxylic acid group, esterification in a fourth step of the second carboxylic acid group, and hydrolysis in a fifth step of the resulting di-ester to isophthalic acid. Such processes are not confined to di-methyl benzenes and for example mesitylene can be converted by the appropriate separate steps to trimesic acid, while 1,4-dimethylnaphthalene can be converted to naphthalene-1,4-dicarboxylic acid.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

LIST OF REFERENCE SIGNS

10-1. First reaction component sources
12. Second reaction component source (suffixes -1 and -3)
14. Motor-operated, micro-agitation means (suffixes -1 through -5, A and B)
15. Motor for micro-agitation means 14 (suffixes -1 through -5, A and B)
16. First reaction component metered pump (suffixes -1 through -5)
18. Second reaction component metered pump (suffixes -1 through -5)
20. Catalytic reaction component metered pump (suffixes -1 and -3)
22. Catalytic reaction component metered pump (suffixes -1 and -3)
24. Flash column for respective process step (suffixes -1 through -3)
26. Recycle feed pump 16 (suffixes -1 through -5)
28. Reservoir receiving previous stage output (suffixes -1 through -3)
30. Reservoir for next step principal reaction component (suffixes -2 through -4)
32. Fourth step crystallizer or drum flaker
34. Fifth step demineralized water source
35. Fifth step reservoir receiving reacted material
36. Cylindrical stator tube
38. Inner cylindrical surface of tube 36
40. Central longitudinal axis of tube 36
42. Cylindrical rotor tube
44. Rotor tube outer cylindrical surface
46. Rotor drive shaft
48. Annular space between the tube surface 38 and rotor surface 44
50. Rotor longitudinal axis when displaced from stator axis 40
54, 56 Inlets to passage 48
58. Outlet from passage 48
60. Annular passage for heat exchange medium
62. Casing providing passage 60
64. Inlet to passage 60
66. Outlet from passage 60

The invention claimed is:

1. The apparatus for the production of materials requiring a plurality of chemical reaction steps:
    wherein the process for which the process apparatus is employed has been separated into a plurality of separate successive process steps, each process step involving the reaction together of at least two principal step reaction components, with or without at least one catalyst component;
    wherein each process step is carried out in a separate, respective process step apparatus comprising:
    motor-operated, micro-agitation means;
    means for feeding the respective principal step reaction components to the motor-operated micro-agitation means wherein they are reacted together while subjected to motion-augmented, sub-Kolmogoroff, micro-agitation to facilitate the reaction between them, the operation of the motor-operated micro-agitation means resulting in a mixture of process step output materials; and
    means for discharging such a mixture therefrom;

and wherein each process step apparatus also comprises:
process step separator means for separating from the mixture of process step output materials received from the micro-agitation means a principal step reaction component for supply to a subsequent process step apparatus;
means for feeding a mixture discharged from the micro-agitation means to the process step separator means; and
means for discharging at least the separated principal step reaction component from the process step separator means for supply to the subsequent process step apparatus.

2. The apparatus as claimed in claim 1, wherein the process includes at least one non-reaction process step employing motion-augmented, sub-Kolmogoroff micro-agitation provided by motor-operated, micro-agitation means, the apparatus including at least one such motor-operated, micro-agitation means disposed in the process sequence at a location selected from the group comprising prior to all of the process steps, prior to any of the process steps involving a reaction, subsequent to any of the process steps involving a reaction, subsequent to all of the process steps, and interposed between any two successive process steps involving a reaction.

3. The apparatus as claimed in claim 2, wherein such motor-operated, micro-agitation means comprises:
a cylindrical stator tube having at least a part along its length of uniform internal diameter about a longitudinal axis to provide a corresponding inner cylindrical surface;
a rotor mounted for rotation within the tube with its longitudinal axis parallel with the tube axis and providing an outer cylindrical surface parallel to the inner tube surface to provide an annular passage between them; and
means for rotating the rotor about its longitudinal axis;
wherein the radial dimension of the passage at most about equal to the combined thicknesses of two boundary layers back-to-back formed on the surfaces with no room between them for an intervening bulk layer such that would permit Taylor vortices to be formed.

* * * * *